(12) United States Patent
Meier et al.

(10) Patent No.: US 8,865,064 B2
(45) Date of Patent: Oct. 21, 2014

(54) METHOD FOR STEAM STERILIZATION OF MEDICAL ARTICLES

(75) Inventors: Andreas Meier, Berlin (DE); Holger Miething, Berlin (DE)

(73) Assignee: Klosterfrau Berlin GmbH, Berlin ( * ) Notice: Subject to any disclaimer, the term of this patent is extended or adjusted under 35 U.S.C. 154(b) by 0 days.

(21) Appl. No.: 14/110,285

(22) PCT Filed: Mar. 21, 2012

(86) PCT No.: PCT/EP2012/001250
§ 371 (c)(1),
(2), (4) Date: Dec. 16, 2013

(87) PCT Pub. No.: WO2012/136313
PCT Pub. Date: Oct. 11, 2012

(65) Prior Publication Data
US 2014/0093422 A1    Apr. 3, 2014

(30) Foreign Application Priority Data

Apr. 7, 2011 (DE) .......................... 10 2011 016 377
Jun. 27, 2011 (DE) .......................... 10 2011 105 840

(51) Int. Cl.
*A61L 2/07* (2006.01)
*A61L 2/04* (2006.01)

(52) U.S. Cl.
CPC ... *A61L 2/04* (2013.01); *A61L 2/07* (2013.01); *A61L 2202/24* (2013.01)
USPC ............................................................ 422/26

(58) Field of Classification Search
CPC .......................................................... A61L 2/07
USPC ............................................................. 422/26
See application file for complete search history.

(56) References Cited

FOREIGN PATENT DOCUMENTS

EP        1484069 A1 * 12/2004

* cited by examiner

*Primary Examiner* — Sean E Conley

(57) ABSTRACT

The invention relates to a method for thermal sterilization in particular of a container filled with medical material or product, the method comprising a sterilization method step in which a thermal sterilization in particular is carried out of a container filled with medical material or product in the presence of a sterilization atmosphere, containing steam, at temperatures of at least 100° C. and at increased pressure, wherein the sterilization method step comprises at least a first method stage and a second method stage, following the first method stage, with first and second method stages being carried out at different pressures with respect to one another, the pressure in the second method stage being increased relative to the pressure in the first method stage.

20 Claims, No Drawings

METHOD FOR STEAM STERILIZATION OF MEDICAL ARTICLES

CROSS-REFERENCES TO RELATED APPLICATIONS

This application is a National Stage filing of International Application PCT/EP 2012/001250, filed Mar. 21, 2012, claiming priority to German Applications No. DE 10 2011 016 377.8 filed Apr. 7, 2011, and DE 10 2011 105 840.4 filed Jun. 27, 2011, entitled "Sterilization of medical instruments for injection and/or instillation." The subject application claims priority to PCT/EP 2012/001250, and to German Applications No. DE 10 2011 016 377.8 and DE 10 2011 105 840.4, and incorporates all by reference herein, in their entirety.

BACKGROUND OF THE INVENTION

The present invention relates to the technical field of sterilization of medical containers, such as medical instruments, ampoules, tubes or the like.

In particular, the present invention relates to a method for thermal sterilization in particular of a container filled with medical material or product, the thermal sterilization being carried out in particular in the presence of a sterilization atmosphere containing steam or under the influence of wet heat.

Furthermore, the present invention relates to the containers, which are obtained according to the method according to the invention, filled with medical material or product and in particular are tubes, ampoules and medical instruments such as e.g. syringes, and to the sterilized filled containers provided in packaging.

Within the scope of the present invention, the term "sterilization" is understood to mean the killing or irreversible inactivation of all microorganisms and viruses, including their rest states, such as e.g. endospores, which are situated on or in an object. Since complete inactivation of all microorganisms and viruses on or in an object cannot be ensured with absolute certainty, an object or a unit of sterilization goods generally counts as sterile if the probability of contamination with microorganisms or viruses that are able to reproduce is no more than $1:10^6$. This means that of one million units of the sterilization goods, at most one unit is contaminated by a colony-forming unit (CFU) of a microorganism or that the remainder of microorganisms or viruses that are able to reproduce is no more than $10^{-6}$ colony-forming units (CFUs) per unit of the sterilization goods. The remainder of at most $10^{-6}$ colony-forming units per unit of sterilization goods is also referred to as sterility assurance level (SAL).

Depending on the type of sterilization goods, different sterilization methods are available, which are distinguished according to chemical and physical sterilization methods.

By way of example, chemical sterilization methods include gassing with formaldehyde or ethylene oxide; however, these are connected with high costs and great methodological-technical expenditure, are only suitable for specific applications as a result of the risks involved in using substances that are hazardous to health and the use of these compounds is not always possible for regulatory reasons. Thus, for example, ready packaging in which the goods to be sterilized are packaged must be permeable to the sterilization gases. However, it must furthermore also be ensured that the gases can once again be completely removed after the sterilization is completed; this proves very difficult in practice. Alternatively, the sterilization goods are sterilized unpackaged, and must subsequently be packaged under sterile conditions, for example in cleanrooms; this increases the complexity and the costs involved in carrying out the method.

Moreover, these methods are not suitable for sterilizing goods stored in sealed containers because no contact can be produced between the sterilization gas and the potential sterilization goods.

Thus, physical methods are generally preferred when selecting the sterilization method if the materials or goods to be sterilized are stable under sterilization conditions. Physical methods have particularly proven their worth in the case of sterilizing packaged sterilization goods or sterilization goods which are situated in sealed containers.

Physical sterilization methods are subdivided into actinic methods, in which the microorganisms are killed or irreversibly inactivated by ionizing radiation, and thermal methods, which are based on thermal exposure.

By way of example, actinic methods include irradiation by UV, gamma or electron beams, which are for example utilized in the industrial production of medical disposable articles.

By contrast, the sterilizing effect of the thermal methods is based on the heat-induced denaturing of proteins, which, along with their native structure, also lose their biological capabilities and effects, resulting in the killing or irreversible inactivation of the microorganisms.

The thermal sterilization methods include, in particular, the hot air sterilization and the steam sterilization, with the hot air sterilization only being suitable for a few applications as a result of the poor reproducibility and the sensitivity towards very small deviations from the ideal method progress, caused by the poor heat transfer of the air.

By contrast, steam sterilization is the "gold standard" of sterilization methods, in which the sterilization goods are as a standard heated by steam at 121° C. and with an overpressure of 2 bar absolute for 15 minutes to a temperature of 121° C. This sterilization method, synonymously also referred to as "saturated steam method", is outstandingly reproducible and automatable and is also suitable for sterilizing goods packaged in sealed containers.

Although the steam sterilization methods have proven their worth in everyday practice and are based on mature technology, the long duration often required for sterilization is disadvantageous; this makes it more difficult to carry out an economically expedient sterilization and increases the costs of actually carrying out the method and, subsequently, of the sterilized products as well. This particularly holds true against the backdrop that steam sterilizations are generally carried out discontinuously in autoclaves. The undesired occurrence of thermal instabilities is also possible.

Shortening the sterilization time, i.e. a more effective sterilization, would lead to a higher throughput and hence to a more economical way of carrying out the method. However, the sterilization temperature would have to be increased significantly for this, which would in turn significantly restrict the selection of sterilization goods to which this method can be applied because plastics in particular can react very sensitively to a temperature increase under the application of humid heat.

Moreover, the conventional steam sterilization methods are disadvantageous in that the amount of energy introduced into the sterilization chamber by the steam is not utilized efficiently. Hence, a large proportion of the energy introduced into the sterilization chamber always remains unutilized as a result of uncondensed steam during steam sterilization methods.

The application of the saturated steam method is primarily restricted by the sensitivity of the materials to be sterilized to humidity and heat. The high effectiveness and efficiency of the saturated steam method is based on the large amounts of energy that are transferred by the steam. Thus: water at 121° C. and a pressure of 2 bar has an enthalpy of vaporization, which is also referred to as latent heat, of 2.199 kJ/kg. When the steam condenses on the cooler sterilization goods, this amount of heat is transferred to the sterilization goods and, if applicable, to the microorganisms situated thereon, as a result of which, firstly, microorganisms are killed or irreversibly inactivated directly and, secondly, sealed containers can be heated such that the contents thereof can also be sterilized—subject to sufficient thermal conductivity and heat transfer in the interior of the container.

Modified steam sterilization methods are applied in the case of sterilization goods, in particular in the case of sealed containers, in the interior of which pressures may build during or, in particular, after the sterilization, more particularly as a result of the filling thereof, which pressures exceed the pressure of the surrounding steam atmosphere. These methods generally do not operate with saturated steam, but rather with steam/air mixtures. As a result of the lower amount of energy in the steam/air mixtures compared to pure steam, these methods are generally carried out in accordance with the standard saturated steam method, which means that steam sterilizations using steam/air mixtures are carried out using longer sterilization times and the sterilization success or the sterilization time is converted to standard conditions (i.e. pure steam at 121° C. and 2 bar absolute) for simpler comparison.

Thus, EP 0 703 793 B1 describes a method for producing sterile ready packaging, with sealed, more particularly blister packed, containers situated therein, more particularly syringes, that are filled with medicines. The sterilization is brought about by means of saturated steam, with the pressure in the sterilization apparatus being increased by means of compressed air during the cooling procedure.

WO 2009/018948 A2 also describes a sterilization method, the disclosed method being intended to be used to sterilize groups of objects and the sterilization taking place by means of steam/air mixtures.

BRIEF SUMMARY OF THE INVENTION

The present invention is therefore based on the object of providing a sterilization method, which at least partly avoids or else at least diminishes the aforementioned problems and disadvantages of the prior art.

More particularly, the present invention is based on the object of providing a sterilization method that has an increased effectiveness or a reduced sterilization time compared to the methods in the prior art.

In particular, a steam sterilization method should be provided, which has greater effectiveness compared to the previously disclosed methods, which more particularly can be carried out with a reduced sterilization time but otherwise operates under "sparing" conditions or conditions that are comparable to the usual method progress.

More particularly, it is a further object of the present invention to provide a container filled with medical goods, which has a reduced number of germs compared to containers filled with medical goods, from the prior art.

In order to achieve the aforementioned object, the present invention proposes a method for sterilization of a medical container filled with a liquid or flowable medical material or product; further advantageous embodiments are provided herein.

A further object of the present invention is a container filled with medical material or product, according to the disclosure herein; further advantageous embodiments are similarly provided.

Finally, a further object of the present invention is a packaging according to the disclosure herein, which provides for a sterilized container filled with medical material or product.

It goes without saying that special refinements, embodiments or the like in the following text, which are only described in conjunction with one aspect of the invention also correspondingly hold true with respect to the other aspects of the invention, without this needing explicit referencing.

Furthermore, it should be noted that all of the following specifications in relative or percentage terms should, within the scope of the present invention, be selected by a person skilled in the art such that this in sum always results in 100%. However, a person skilled in the art considers this self evident.

Moreover, a person skilled in the art may in relation to applications or in individual cases deviate from the number, region or amount specifications listed below, without departing from the scope of the present invention.

Moreover, all parameter specifications or the like specified in the following text can in principle be determined or established with standardized or explicitly specified determination methods or else with determination methods known per se to a person skilled in the art.

DETAILED DESCRIPTION OF THE INVENTION

Hence, according to a first aspect of the present invention, an object of the present invention is a method for thermal sterilization in particular of a container filled with medical material or product, the method comprising a sterilization method step in which a thermal sterilization in particular is carried out of a container filled with medical material or product in the presence of a sterilization atmosphere, containing steam, at temperatures of at least 100° C. and at increased pressure, wherein the sterilization method step comprises at least a first method stage and a second method stage, following the first method stage, with first and second method stages being carried out at different pressures with respect to one another, the pressure in the second method stage being increased relative to the pressure in the first method stage.

This is because, as surprisingly determined here, the effectiveness of the sterilization and the rate of killing or irreversible inactivation of microorganisms can be significantly increased by a pressure increase in a subsequent second method stage of the sterilization method step, with it being possible to carry out the sterilization at comparatively mild method conditions.

As a result of increasing the pressure during the sterilization method step, more particularly during the subsequent second method stage, the condensation of the steam on the sterilization goods is improved or optimized, which leads to better use of the energy contained in the system as a result of additional heat transfer. Hence the method according to the invention, at the same sterilization temperature, can achieve improved killing or irreversible inactivation of the microorganisms or a reduced sterilization time compared to steam sterilization methods in the prior art.

Hence, within the scope of the present invention it is possible to reduce the sterilization time under sparing conditions because the method according to the invention can be used to sterilize the same sterilization goods and materials as in the standard saturated steam method or methods with steam/air mixtures, i.e. the method according to the invention does not have increased requirements in respect of the heat resistance of the goods or materials to be sterilized.

Moreover, the method according to the invention also intrinsically has all of the advantages of the conventional steam sterilization methods. Thus, for example, the method according to the invention can also be used to sterilize goods in sealed containers or accordingly embodied ready packaging. Hence the method according to the invention dispenses with a complicated and also time and cost intensive filling of the containers with goods for the medical application in sterile conditions.

The method according to the invention is moreover outstandingly reproducible and can be automated without problems. In particular, the method according to the invention makes possible continuous simultaneous monitoring of the sterilization and also a quick and targeted adjustment of the method to the respective progress of the sterilization.

The sterilization atmosphere containing steam, used within the scope of the method according to the invention, may be a saturated steam atmosphere, an atmosphere of superheated steam or else a mixture of gases, more particularly inert gases and/or air, and steam.

Within the scope of the present invention, "increased pressure" should be understood to mean the pressure in a gaseous phase, which is greater than the pressure under standard conditions (1.013 bar at 25° C.) or the pressure of the surrounding atmosphere (generally approximately 1 bar). It follows that an increased pressure can be characterized or captured by a positive magnitude of the relative pressure.

Within the scope of the present invention, the "relative pressure" of a system is understood to mean the pressure difference between the absolute pressure of the gaseous phase of the relevant system (e.g. the pressure within an autoclave) and the absolute pressure of the surrounding atmosphere.

Within the scope of the present invention, "medical material or product" more particularly are medicines, pharmaceuticals and medical products. By way of example, the containers utilized according to the invention and filled with medical material or product are syringes filled with catheter gel or the like.

In respect of the first and the second method stage of the sterilization method step of the method according to the invention, the second method step can directly follow the first method step. However, it is also possible for further method stages to lie between the first and the second method stage, the respective pressures of which further method stages may differ from the first and/or the second method stage.

It is furthermore important that within the scope of the present invention, the container to be sterilized is filled with the medical material or product before the method according to the invention starts and, more particularly, in non-sterile conditions. Hence, within the scope of the present invention, it is not only the outer surface of the container that is intended to be sterilized, but rather also the medical material or product situated within the container.

The sterilization method step of the method according to the invention more particularly merely comprises the period of time during which the sterilization goods are at the desired sterilization temperature or in which the temperature of the sterilization goods is situated within the temperature range predetermined for the sterilization.

In general, within the scope of the present invention, provision is made for a heating method step to precede the sterilization method step and/or for a cooling method step to follow the sterilization method step. Here, the heating method step comprises both the actual heating phase (also referred to as rise time), during which the temperature of the sterilization atmosphere is reached, and also the so-called compensation time which is required in addition to the heating phase. The compensation time (synonymously also referred to as "plateau time") describes or defines the period of time required for the complete warming of the sterilization goods to the desired sterilization temperature.

According to a special embodiment, the present invention relates to a method for thermal sterilization in particular of a container filled with medical material or product, more particularly as described above, the method comprising (a) optionally a heating method step; then
(b) a sterilization method step in which a thermal sterilization in particular is carried out of a container filled with medical material or product in the presence of a sterilization atmosphere, containing steam, at temperatures of at least 100° C. and at increased pressure; then
(c) optionally a cooling method step, wherein the sterilization method step (b) comprises at least a first method stage and a second method stage, following the first method stage, with first and second method stages being carried out at different pressures with respect to one another, the pressure in the second method stage being increased relative to the pressure in the first method stage.

Within the scope of the present invention, provision can be made for the sterilization method step to be carried out in the presence of an atmosphere containing pure steam and/or as a saturated steam method. Here, saturated steam should be understood to mean a saturated atmosphere of pure steam (wherein pure steam, more particularly pursuant to European Norm EN 285 may contain up to 3.5% by volume of non-condensable gases such as oxygen, nitrogen, etc), while an atmosphere containing pure steam may for example also be an atmosphere made of superheated steam.

However, particularly good results are also obtained within the scope of the present invention if the sterilization method step is carried out in the presence of a steam/gas mixture, more particularly a mixture of steam with nitrogen and/or oxygen and/or inert gases, preferably a steam/air mixture. Here, steam/gas mixtures can be produced by separate or combined addition of gas and steam, the composition of the steam/gas mixtures, i.e. the respective components of steam and gas or air, not being critical and being able to be varied with almost no restrictions. In the case of steam/air mixtures, care has to be taken that there is deep, preferably continuous circulation or mixing because these otherwise un-mix, which would endanger the success of the sterilization.

In general, the method is carried out in a closed sterilization apparatus, more particularly in a gas-tightly sealed pressure container, preferably in an autoclaving apparatus (autoclave).

In this context, it was found to be advantageous for the sterilization atmosphere to be produced by injecting steam and/or steam/compressed air mixtures, preferably steam/compressed air mixtures, into the sterilization apparatus.

In the process, it was found to be advantageous if the sterilization atmosphere is produced by injecting already premixed steam/compressed air mixtures and/or by respectively separate injections of steam and compressed air into the sterilization apparatus. The injection of already premixed steam/compressed air mixtures is easier to carry out from a technical stand point but only allows a restricted adaptation to the respective method progress. The separate injection of steam and gas or compressed air is advantageous in that the individual parameters of the sterilization atmosphere, such as pressure, temperature or composition, can be set and individually regulated in an improved and simpler fashion, and so there can be an individual response to the respective method progress and the method overall can be adapted to different requirement profiles without problems. Thus, according to the invention, the separate injection of steam and compressed air or gas into the sterilization apparatus is preferred.

To an equal extent, it was found to be advantageous within the scope of the present invention if the steam is produced from distilled and/or demineralized water or if the compressed air is produced from sterile air. Here, provision is advantageously made in particular for the air to be cleaned and/or sterilized by flowing through filters. Here, as filters, use is in particular made of particulate filters, which can separate out objects of the order of less than 1 μm in general, but in particular of greater than 0.2 μm, such as e.g. HEPA filters (high efficiency particulate air filters), ULPA filters (ultra low penetration air filters) and SULPA filters (super ultra low penetration air filters). Using sterilized air is advantageous in that no additional microorganisms are introduced into the sterilization apparatus and contamination of the sterilization goods by increasing the initial number of germs can be excluded. The use of demineralized or distilled water for generating the steam firstly spares the sterilization apparatus and also the inflow and outflow lines thereof and secondly prevents the deposition of residues or salts on the sterilization goods.

In general, the sterilization method step is carried out in a temperature range of between 100 and 180° C., more particularly between 100 and 150° C., preferably between 105 and 145° C., particularly preferably between 105 and 140° C., very particularly preferably between 110 and 135° C., even more preferably between 110 and 130° C. In these temperature ranges, the sterilization method according to the invention can be carried out effectively within acceptable time periods and is suitable for a multiplicity of materials.

In general, the sterilization method step is carried out over a period of time of between 0.1 and 600 minutes, more particularly between 0.5 and 300 minutes, preferably between 1 and 100 minutes, more preferably between 2 and 60 minutes, particularly preferably between 3 and 45 minutes, even more preferably between 4 and 30 minutes, very particularly preferably between and 20 minutes, most preferably between 5 and 15 minutes. Hence, the method according to the invention renders it possible to carry out the sterilization in reduced sterilization times compared to the standard saturated steam method—and this at comparable temperatures.

In respect of the time duration of the individual method stages of the sterilization method, it was found to be advantageous within the scope of the present invention if 20 to 95%, more particularly 40 to 90%, preferably 50 to 85%, particularly preferably 60 to 80% of the time duration of the sterilization method step is allotted to the first method stage of the sterilization method step and/or if 5 to 80%, more particularly 10 to 60%, preferably 15 to 50%, particularly preferably 20 to 40% of the time duration of the sterilization method step is allotted to the second method stage of the sterilization method step.

Likewise, particularly good results are obtained if the sterilization method step is carried out in a relative pressure range of between 0.05 and 10 bar, more particularly between 0.1 and 4 bar, preferably between 0.5 and 3.5 bar, particularly preferably between 1 and 3.25 bar, even more preferably between 1.5 and 3 bar, very particularly preferably between 2 and 2.8 bar. In other words, the sterilization method step can in particular be carried out in an absolute pressure range of between 1.05 and 11 bar, more particularly between 1.1 and 5 bar, preferably between 1.5 and 4.5 bar, particularly preferably between 2 and 4.25 bar, even more preferably between 2.5 and 4 bar, very particularly preferably between 3 and 3.8 bar. Sufficient condensation of the steam on the sterilization goods is ensured in these pressure ranges and use can for example be made of steam/air mixtures that are particularly suitable for effective sterilization.

When carrying out the method according to the invention, it has proven to be advantageous if the relative pressure at the start of the sterilization method step is set to a value of at least 1 bar, more particularly at least 1.2 bar, preferably at least 1.5 bar, more preferably at least 2 bar. In particular, the absolute pressure at the start of the sterilization method step can be set to a value of at least 2 bar, more particularly at least 2.2 bar, preferably at least 2.5 bar, more preferably at least 3 bar. At these pressures there is very good heat transfer onto the sterilization goods by the steam, and so outstanding sterilization results can be achieved in an overall short sterilization time.

Here, the precise setting for the pressure during the sterilization method step, more particularly at the start of the sterilization method step, depends on the respective method conditions such as the composition of the sterilization atmosphere or the materials to be sterilized: if use is made of a sterilization atmosphere of saturated steam in the first stage of the sterilization method step, it was found to be advantageous if the relative pressure at the start of the sterilization method step is set in the region of 1 to 1.5 bar or if the absolute pressure at the start of the sterilization method step is set in the region of 2 to 2.5 bar.

By contrast, if a steam/gas mixture, more particularly a steam/air mixture, is used in the first method stage of the sterilization method step, the pressure can vary over large regions, in particular within the aforementioned general regions.

However, in addition to the magnitude of the pressure, the duration of the respective pressure application also influences the method progress.

Thus, within the scope of the present invention, during the sterilization method step, provision can be made for the relative pressure to exceed a value of 1 bar, more particularly 1.2 bar, preferably 1.5 bar, more preferably 2 bar, for at least some of the time, more particularly for a period of time of at least 10%, more particularly at least 20%, preferably at least 30%, particularly preferably at least 40%, very particularly preferably at least 50%, of the overall time of the sterilization method step and most preferably for the entire duration of the sterilization method step.

Hence, during the sterilization method step, provision can be made for the absolute pressure to exceed a value of 2 bar, more particularly 2.2 bar, preferably 2.5 bar, more preferably 3 bar, for at least some of the time, more particularly for a period of time of at least 10%, more particularly at least 20%, preferably at least 30%, particularly preferably at least 40%, very particularly preferably at least 50%, of the overall time of the sterilization method step and most preferably for the entire duration of the sterilization method step.

It is preferable within the scope of the present invention for the aforementioned pressures and time intervals to be adhered to because this allows reliable killing of the germs—as a result of the high temperature and the good heat transfer—at practicable and acceptable method durations. In the process, it is particularly preferred if the aforementioned pressures are maintained over the entire duration of the sterilization method step.

Particularly good results are obtained within the scope of the present invention if the relative pressure at the end of the sterilization method step is set to values of less than 4 bar, more particularly less than 3.5 bar, preferably less than 3.25 bar, more preferably less than 3 bar, very particularly preferably less than 2.8 bar and if the absolute pressure at the end of the sterilization method step is set to values of less than 5 bar, more particularly less than 4.5 bar, preferably less than 4.25 bar, more preferably less than 4 bar, very particularly preferably less than 3.8 bar.

In general, the relative pressure increase from the first to the second method stage of the sterilization method step is at least 0.01 bar, more particularly at least 0.05 bar, preferably at least 0.1 bar, more preferably at least 0.15 bar, particularly preferably at least 0.2 bar, very particularly preferably at least 0.25 bar.

In this context, it was found to be particularly advantageous if the relative pressure increase between the first and the second method stage of the sterilization method step is in the region of 0.01 to 2 bar, more particularly in the region of 0.05 to 1 bar, preferably in the region of 0.1 to 0.75 bar, more preferably in the region of 0.15 to 0.5 bar, even more preferably in the region of 0.2 to 0.4 bar. In this pressure range, the pressure increase has a significant impact in terms of increased effectiveness and reduced duration of the sterilization but likewise still allows the method to be carried out in an economically expedient fashion and moreover does not put an excessive load on the sterilization goods or the utilized materials.

According to a particularly preferred embodiment of the present invention, the pressure increase between the first and second method stage of the sterilization method step is brought about by introducing gas, more particularly air, preferably compressed air. Herein it is once again advantageous if the gas, more particularly the air, preferably the compressed air, is sterile.

A pressure increase as a result of gas, more particularly air, preferably compressed air, in the second method stage of the sterilization method step or in the transition between the first and the second method stage in particular allows the optimum utilization of the energy contained in the steam as a result of an improved or optimized condensation of the steam since, at the same time, the additional energy input into the sterilization apparatus by the gas or the compressed air is only very small compared to the steam. Thus, optimal utilization of the advantages obtained by the pressure increase is realized by applying pressure by means of gas, more particularly air, preferably compressed air.

Within the scope of the method according to the invention, provision can be made for the sterilization method step to comprise 2 to 10 method stages, with at least 2 method stages being carried out at different pressures. Here, provision can in particular be made for the pressure to be increased in a subsequent method stage compared to the pressure in a preceding method stage.

Within the scope of the present invention, it is particularly preferred if the sterilization method step merely consists of two method stages, with the pressure increase between the first and the second method stage being brought about by a pressure increase by means of compressed air, more particularly in the form of one or more compressed-air blasts, preferably one compressed-air blast. The use of compressed-air blasts, more particularly a single compressed-air blast, makes a rapid increase of the pressure within the sterilization apparatus possible and leads to the immediate onset of improved condensation of the steam. The compressed-air blast or the compressed-air blasts are preferably carried out using compressed air, with the temperature of the sterilization atmosphere by all means being allowed to fall after the compressed air was introduced; however, it is essential that the temperature of the sterilization goods remains at the set sterilization temperature for the intended sterilization duration or is situated in the temperature interval (i.e. the predetermined temperature band or temperature regime) that is wanted and needed for the sterilization.

Very good results can be obtained within the scope of the present invention if the first method stage of the sterilization method step is carried out in the form of a saturated steam method and the pressure loading or pressure increase from the first to the second method stage is brought about using sterile compressed air. This specific method is for example suitable for the sterilization of containers filled with medical material or product, in which no high pressure builds up during the sterilization or which can withstand high internal pressure without damage.

Moreover, very good results are obtained within the scope of the present invention if the first method stage of the sterilization method step is carried out in a sterilization atmosphere made of a steam/gas mixture, more particularly a steam/air mixture and if the pressure loading or pressure increase from the first to the second method stage is brought about using sterile compressed air. This type of method allows a much broader and comprehensive application of the method according to the invention than the use of a sterilization atmosphere of saturated steam in the first method stage of the sterilization method step because a pressure build-up in the interior of the containers to be sterilized can be counteracted. By way of example, syringes filled with liquids can be sterilized when using a sterilization atmosphere of a steam/air mixture.

In general, when the method according to the invention is carried out, it is possible, at least during the sterilization method step, preferably during the entire method duration, for the method to be controlled and/or monitored by measuring and regulating pressure and/or temperature (more particularly by measuring and regulating pressure and/or temperature only), preferably pressure and temperature, more particularly pressure and temperature of the sterilization atmosphere and optionally the temperature of at least one reference sample situated in the sterilization apparatus, more particularly of a plurality of reference samples situated in the sterilization apparatus. In principle, the method according to the invention can also be carried out without such reference samples. According to the invention, it is preferable if the control and/or monitoring of the method is exclusively carried out by measuring and controlling at least one of the two aforementioned parameters (i.e. pressure and/or temperature).

Until now, it was conventional in the prior art—if at all—to determine temperature and humidity of the sterilization atmosphere, with the temperature of reference samples additionally being determined if need be. However, precisely the humidity measurement was found to be particularly imprecise and difficult to monitor from a measurement-technical point of view and often leads to incorrect values.

Within the scope of the present invention, a reference sample should more particularly be understood to mean a control sample, which is preferably a structurally identical or at least similar or comparable (i.e. it can be correlated) container to the sterilization goods with the same material or product, but which is provided with a sensor or an apparatus for measuring or determining the temperature of the material or product.

Moreover, it was found to be advantageous within the scope of the present invention if, at least during the sterilization method step, preferably during the entire method, pressure and/or temperature, preferably pressure and temperature, more particularly pressure and temperature of the sterilization atmosphere and optionally the temperature of at least one reference sample situated in the sterilization apparatus, more particularly of a plurality of reference samples situated in the sterilization apparatus, are determined and optionally set, more particularly to predetermined values.

Particularly good results are obtained if the pressure and temperature data are used to monitor and/or control at least the sterilization method step, preferably the entire method.

The established data first of all permit retrospective monitoring of the sterilization procedure and adequate archiving of the results; however, concurrent monitoring of the sterilization procedure is also possible such that there can be a rapid adaptation of the method as a result of the established measurement values. As a result, the method can firstly be adapted to specific conditions of the products in an individual and flexible fashion; secondly this also allows a quick reaction to problems occurring during the sterilization method, and so these can already be rectified during the sterilization. This avoids or reduces the risk of insufficient sterilizations with the coupled high economic loss.

In general, the method according to the invention is carried out in accordance with the standard saturated steam method, more particularly as so-called $F_0$-value method, or the method is carried out in the form of an overkill method. However, the method according to the invention can alternately also be carried out in a product-specific fashion, taking into account an expected and/or an experimentally determined number of germs and/or type of germ.

In the case of the standard saturation steam method, the sterilization goods are heated for 15 minutes to 121° C., as a result of which there is a reduction in the initial germ number from $10^4$ to a value of $10^{-6}$, corresponding to the sterility assurance level (SAL). The sterilization time of 15 minutes also already contains a safety supplement, which should ensure that the sterilization success is actually achieved.

In the equivalence methods or the sterilization methods carried out in accordance with the standard saturation steam method, the so-called $F_0$-value is calculated; it specifies how many minutes an object is sterilized equivalently to 121° C. A germ reduction from $10^4$ to $10^{-6}$ per unit of the sterilization goods should also be achieved in the equivalence methods or the sterilization methods carried out in accordance with the standard saturation steam method, with however, deviating from the standard method, e.g. another temperature being selected or a different value being achieved in the energy transfer as a result of using steam/air mixtures. Converting to standard conditions and specifying the $F_0$ value allow an immediate and simple comparison or an assessment of the sterilization success, in which the data required for the conversion or the conversion factors can, depending on the precise methodology, either be gathered from appropriate reference works or else have to be determined experimentally. Both in the standard saturated steam method and in the corresponding $F_0$-value methods, such as the equivalence method, the sterilization success must be detected or documented by regular monitoring.

The overkill method differs from the standard or equivalence method in that an initial germ number of $10^6$ is assumed per unit of the sterilization goods, i.e. a 100 times higher germ load than in the standard or equivalence method, which load should be reduced to a value of $10^{-6}$. This safety supplement by assuming a higher germ load allows for longer intervals when determining the actual germ load or the germs actually occurring on the sterilization goods, and also the sterilization success.

When carrying out the method according to the invention in a product specific fashion, the number of germs to be expected at the start on the non-sterilized sterilization goods and the type of germs to be expected are determined experimentally and these data are used to carry out the method such that a reduction in the germ load to $10^{-6}$ is achieved. This makes it possible to achieve significantly shorter sterilization times; however, there are stringent requirements on the continuous monitoring of the types of germs and germ numbers on the sterilization goods, which is the so-called bio-burden monitoring.

As explained above, the method according to the invention usually comprises a heating method step.

In this context, it has proven its worth within the scope of the present invention if, during the heating method step, pressure and/or temperature, more particularly pressure and temperature, of the atmosphere within the sterilization apparatus are modified, more particularly increased, more particularly modified in a continuous and/or discontinuous fashion.

In this context, particularly good results are obtained if the heating method step is subdivided into at least 2 method stages, preferably into 2 to 10 method stages, and the pressure in the sterilization apparatus in a subsequent method stage, compared to the pressure in a directly preceding method stage, is reduced, more particularly by evacuation, or increased, more particularly by introducing steam and/or gas, more particularly compressed air.

During the heating method step, pressure and temperature can be increased or reduced in any sequence or succession, particularly with the stipulation that pressure and temperature at the end of the heating method step correspond to the conditions for the actual sterilization method step.

In general, the sterilization atmosphere used in the first method stage of the sterilization method step is produced during the heating method step. This allows the sterilization method step to directly adjoin, i.e. without intermediate stages, the heating method step.

Within the scope of the present invention, the heating method step more particularly also comprises the so-called compensation time, i.e. the time required to completely heat the sterilization goods through after the temperature in the sterilization apparatus has already reached the predetermined value for the sterilization method step. Within the scope of the present invention, the heating method step thus comprises the rise time and the compensation time.

A person skilled in the art is aware of a multiplicity of methods for heating the sterilization apparatus and for generating the sterilization atmosphere: thus, for example, the gravitation method can be used to replace the heavier air with lighter hot steam. However, a higher purity of the sterilization atmosphere is achieved by vacuum methods. In the simplest case, such a vacuum method consists of a simple pre-vacuum and a subsequent pressure increase by means of steam or a steam/air mixture. However, even better results are obtained by a fractionated vacuum, with the fractionated vacuum methods being subdivided into sub-atmospheric, super-atmospheric and trans-atmospheric vacuum methods. The fractionated vacuum methods can moreover be combined with vacuum/overpressure cycles, in which the pressure is firstly increased and then reduced again in order subsequently to be increased to a higher value than during the preceding pressure increase such that overall this results in a pressure increase.

Within the scope of the present invention, use is preferably made of a fractionated vacuum, optionally in combination with vacuum/overpressure cycles. Here, it is furthermore preferred if the individual pressure increases during the fractionated vacuum methods and optionally during the vacuum/overpressure cycles are brought about by means of saturated steam and if these methods are carried out such that at least 95% of the original atmosphere is replaced.

In general, it is conventional in the method according to the invention that, during the cooling method step, the container filled with medical material or product is cooled and dried and/or that, during the cooling method step, pressure and/or temperature, more particularly pressure and temperature, of the atmosphere within the sterilization apparatus are modified, more particularly decreased, more particularly modified in a continuous and/or discontinuous fashion.

In this context, provision can be made for the cooling method step to be subdivided into at least 2 method stages, preferably into 2 to 10 method stages.

As likewise explained above, the method according to the invention usually comprises a cooling method step.

Particularly good results are obtained if, during the cooling method step, an increased pressure, more particularly a supporting pressure, is applied at least temporarily, preferably such that the pressure present in the container filled with medical material or product is counteracted.

Here, within the scope of the present invention, a supporting pressure should more particularly be understood to mean additional pressure application during the cooling method step, preferably by means of compressed air, which counteracts an expansion of the still hot material or product or of the gas present in the container while the temperature of the atmosphere in the sterilization apparatus is already sinking and inducing a reduction in pressure.

Advantageously, the cooling method step is carried out such that pressure and temperature are alternately increased and reduced such that the condensed water is returned to the gaseous phase and can be removed from the sterilization apparatus. By way of example, the temperature in the sterilization apparatus is briefly increased for this purpose. Hence, the cooling method step is carried out so as to complement the likewise preferred vacuum/overpressure cycles during the heating method step; however, the additional supporting pressure counteracts an expansion of the material or product.

At the end of the cooling method step, more particularly after reaching a predetermined final temperature, the sterilized container filled with the medical material or product is advantageously subjected to pressure being applied, more particularly with a relative pressure in the region of 0.5 to 10 bar, more particularly 1 to 5 bar, preferably 1.5 to 3 bar. Particularly in the case of syringes, such as piston syringes, this ensures that reduced pressure in the interior of the container is effectively counteracted.

In the special case of a piston syringe, this moreover brings the piston into an application-ready position such that application errors can be avoided.

In general, within the scope of the present invention, provision is made for the medical material or product to be liquid and/or flowable. Thus, liquid-based materials or products, such as e.g. liquids, gels or pastes, are preferably used within the scope of the present invention. However, this type of material or product constitutes a particular challenge to the method progress because the materials or products can contribute to pressure building up within the container by partial evaporation of the liquid or by entrapped gases. It is for this reason that sterilization by means of steam/air mixtures is preferred within the scope of the present invention and the application of a supporting pressure is advantageous during the cooling method step.

Likewise, provision can be made for the medical material or product to be a medicine, pharmaceutical or medical product, more particularly a lubricant, preferably a catheter lubricant.

In general, the container used within the scope of the present invention is a medical container, more particularly an ampoule, a tube or a medical instrument, more particularly a catheter or a syringe, preferably a bellows-type syringe or a piston syringe, more preferably a piston syringe.

Particularly good sterilization results are obtained within the scope of the present invention if the container is a piston syringe, more particularly a disposable piston syringe, preferably made of plastic, more preferably a piston syringe with a cylindrical cavity or base body, which has an opening for holding a piston at one end and a nozzle at the opposite end.

As per a preferred embodiment according to the invention, the container filled with medical material or product is a piston syringe filled with a catheter lubricant, preferably a disposable piston syringe, preferably made of plastic.

The container, more particularly the medical container, preferably the syringe, which is used within the scope of the present invention, can consist of a multiplicity of materials, more particularly plastics materials but also glass-containing materials; the only conditions placed upon these materials are that they are suitable and licensed for medical applications and moreover are stable under method conditions, in particular under increased pressure and increased temperature.

Within the scope of the present invention it was found to be particularly advantageous if the container, more particularly the medical container, preferably a syringe, consists of heat-resistant materials, more particularly of materials that withstand temperatures in the range of 100 to 150° C., more particularly temperatures up to 140° C., preferably up to 135° C., more preferably up to 130° C. In the process, it was found to be particularly advantageous if the container, more particularly the medical container, preferably a syringe, partly or wholly, preferably wholly, consists of heat-resistant plastics materials or glass materials.

According to a special embodiment of the present invention, provision can be made for a multiplicity of containers filled with medical material or product to be sterilized at the same time; here, during the method, a plurality of containers can be brought together on a carrier or combined to form a unit. This way of carrying out the method according to the invention in particular permits the sterilization of a multiplicity of containers, as a result of which the sterilization apparatus can be loaded with a large number of containers. This can increase the throughput of the sterilization method.

According to a preferred embodiment of the present invention, provision is made for the container filled with medical material or product to be introduced into tightly closed and/or sealed packaging, more particularly ready packaging, with at least part of the packaging being designed to be at least permeable to steam, more particularly permeable to steam and/or permeable to gas. In this context, it was found to be advantageous if the packaging is sterilized to the same extent. Such ready packaging, as for example formed by a blister pack, in general consists at least in part of a sterilization paper, which permits the passage of steam and hence direct contact between steam and container to be sterilized.

According to a second aspect of the present invention, a further object of the present invention is a container filled with medical material or product, which was sterilized as per the above-described method.

Compared to the standard saturated steam method and the methods according to the prior art, the container according to the invention, filled with medical material or product, is distinguished by a reduced number of germs in the case of the same sterilization time or by sterility in significantly reduced sterilization times.

In general, the container according to the invention is a medical container, more particularly an ampoule, a tube or a medical instrument, more particularly a catheter or a syringe, preferably a bellows-type syringe or a piston syringe, preferably a piston syringe.

As per a preferred embodiment of the present invention, the container is a piston syringe, more particularly a disposable piston syringe, preferably made of plastic, more preferably a piston syringe with a cylindrical cavity or base body, which has an opening for holding a piston at one end and a nozzle at the opposite end.

In this context, provision can be made for the container filled with medical material or product to be a piston syringe filled with a catheter lubricant, preferably a disposable piston syringe, preferably made of plastic.

According to a particularly preferred embodiment of the present invention, the container is a syringe, more particularly a piston syringe, the syringe having a hollow cylindrical base body which has an opening for holding a piston at one end and a nozzle at the opposite end, and comprising a piston that can move in the cavity of the cylindrical base body, parallel to the direction of extent of the cylindrical base body, the cavity of the cylindrical base body being filled with medical material or product, more particularly with a liquid and/or flowable medical material or product, and the nozzle being optionally sealed and/or blocked.

Here, it was found to be advantageous within the scope of the present invention if the proportion or the volume of the gas in the cavity of the syringe is minimized or if the syringe is filled in a vacuum. The gas expands during the thermal sterilization and thus generates a pressure on the internal walls of the container or on the material or product. The container, more particularly the syringe, is therefore advantageously filled such that the expansion or the volume of the gas and/or air bubbles remaining in the cavity of the container, more particularly of the syringe, during the filling is minimized, more particularly preferably such that no gas and/or air bubbles remain in the cavity of the container, more particularly of the syringe.

By way of example, the gas volume remaining in the cavities of the syringes can be minimized by an optimized geometry of base body and piston such that the piston fills the cavity of the base body to the greatest possible extent in the unfilled state.

Within the scope of the present invention it was found to be advantageous if the syringe is filled through the nozzle, with the volume enclosed by the cylindrical base body of the syringe and the moveable piston being minimized at the start of the filing and being expanded to the desired amount by moving the piston along the axis of the base body while the material or product is being filled. This can achieve particularly even and homogeneous filling of the syringe body, which moreover spares resources. Here, the syringe can be filled by pressing the material or product into the cavity of the syringe or else by exerting a pulling force on the piston of the syringe. However, as an alternative thereto, the syringe can also be filled via the piston opening side, which lies opposite the nozzle of the syringe; this filling should be carried out under reduced pressure in order to avoid air being trapped.

Furthermore, the nozzle of the syringe can be provided with a rigid, more particularly pressure-resistant closure. This means that the closure of the nozzle, optionally by means of support by a supporting pressure, counteracts an expansion of the material or product.

However, provision can alternatively also be made for the nozzle of the syringe to be provided with a flexible closure. Such a flexible closure allows the material or product to expand within defined limits, and so there can be a significantly lower application of a supporting pressure than in the case of a rigid closure of the nozzle. Moreover, a particular embodiment of the flexible closure can ensure a reduction in pressure, i.e. the flexible closure in this embodiment allows slight opening of the nozzle in order to reduce the pressure. By way of example, this means that a remaining gas volume, possibly situated in the cavity of the syringe, can expand. However, in all embodiments with a flexible closure, it is imperative to ensure at all times that the material or product does not escape from the container, more particularly the syringe, neither during the sterilization nor during storage. Moreover, such a flexible closure may not lead either to an increased risk of recontamination or to a reduced shelf life of the container, for example as a result of the egress of moisture or solvents.

In respect of more in-depth details in respect of this aspect of the invention, reference may be made to the preceding explanations in respect of the method according to the invention, which explanations analogously also hold true for the container according to the invention.

Finally, according to a third aspect of the present invention, an in turn further object of the present invention is packaging, more particularly packaging sterilized according to the above-described method, containing a sterilized container filled with medical material or product, more particularly a syringe, as described above.

In respect of more in-depth details in respect of this aspect of the invention, reference may be made to the preceding explanations in respect of the method according to the invention and the container according to the invention, which explanations analogously also hold true for the packaging according to the invention.

Further embodiments, developments and variations of the present invention are readily identifiable and implementable by a person skilled in the art when reading the description, without said person skilled in the art departing from the scope of the present invention in the process.

The present invention is exemplified on the basis of the following exemplary embodiments; however, these are in no way intended to restrict the present invention.

EXEMPLARY EMBODIMENTS 97 15 ml-disposable plastic syringes are respectively filled with 11 ml of a catheter lubricant under non-sterile conditions, with 10 randomly selected samples respectively being contaminated with at least $10^6$ spores of *Geobacillus stearothermophilus*. The nozzles of the syringes are respectively closed by a closure cap and the actual germ load of 20 further syringes, selected at random, is determined before the method is carried out, with it being possible to detect an infestation of microorganisms in all 20 systems.

The syringes are subsequently welded into blister packs, the rear sides of which consist of sterilization paper that is permeable to steam.

Three further syringes, which are filled with the catheter lubricant, are equipped with a temperature sensor that continuously measures the temperature of the catheter lubricant and routes the data to the central computer for controlling the sterilization method. These three samples are also subsequently blister packed.

The overall 100 samples are now introduced into a sterilization apparatus and subjected to a sterilization method consisting of a heating method step, a sterilization method step and a cooling method step.

At the start of the method, the atmosphere present in the sterilization apparatus is exchanged and replaced by the sterilization atmosphere while heating by firstly applying a fractionated sub-atmospheric vacuum, i.e. the sterilization apparatus is repeatedly evacuated to a negative pressure of 1 bar (relative pressure of −1 bar) and the pressure is subsequently returned to approximately ambient pressure by blasts of steam. The sterilization atmosphere, which consists of a steam/air mixture, is subsequently generated by alternating steam and compressed-air blasts and brought to a temperature of 123° C. and a relative pressure of 2.3 bar.

The pressure and the temperature of the atmosphere in the sterilization apparatus are established throughout the entire method duration. Likewise, the temperature of the sterilization goods is also determined using the three reference samples respectively equipped with a temperature sensor.

After the compensation time has elapsed, the actual sterilization method step starts at a reference sample temperature of 120° C. The temperature of the sterilization atmosphere is kept at 123° C. for 10 minutes, with the relative pressure being 2.3 bar.

After the 10 minutes have passed, the pressure in the sterilization apparatus is increased by 0.2 to 0.5 bar by a single compressed-air blast, as a result of which there is increased or boosted condensation of the steam and corresponding increased utilization of the energy found in the steam.

The stage of the sterilization method step under increased pressure is maintained for a total of 3 minutes, during which the temperature in the sterilization atmosphere may fall, but not the temperature in the sterilization goods. Hence, the actual sterilization method step extends over a period of time of 13 minutes.

The multistage cooling method step follows the sterilization method step. The temperature of the atmosphere in the sterilization apparatus is firstly cooled to approximately 40° C. in a three-stage process, with the pressure in the sterilization apparatus being kept constant throughout by a supporting pressure and being approximately 2.6 bar (relative). During this time, the temperature of the sterilization goods sinks to approximately 80° C. This cooling process is followed by a multistage drying process, during which the temperature of the atmosphere in the sterilization apparatus is repeatedly increased and the pressure is simultaneously reduced in the sterilization apparatus in order to return the condensed water into the gaseous phase. The pressure is subsequently increased again in order to counteract an expansion of the catheter lubricant in the syringes.

This procedure is repeated until there is no condensed water left in the sterilization apparatus.

The pressure within the sterilization apparatus is subsequently once again set to approximately 2 bar relative by means of compressed air, the sterilization apparatus is ventilated and opened.

Blister packs and syringes are subsequently examined for mechanical damage or leaking of the catheter lubricant. However, all samples were in a faultless condition.

The 97 blister-packed syringes are subsequently unpacked under sterile conditions and both the syringes and also the catheter lubricant and blister packs are examined in respect of microorganisms. It was not possible to detect a contamination with microorganisms in any of the samples, not even in the 10 selected samples to which spores of *Geobacillus stearothermophilus* were added.

Further trials determined that the 13 minute sterilization method step of the above-described method corresponds to an 18 minute sterilization under standard conditions, i.e. the performed method according to the invention has an $F_0$ value of 18.

For comparison purposes, trials that are analogous to the method according to the invention are carried out, in which merely the additional pressure loading during the sterilization phase has been dispensed with. An $F_0$ value of 15.5 can be established for the sterilization method carried out thus. Moreover, spores that are still capable of reproducing could be detected in two of the samples contaminated with spores of *Geobacillus stearothermophilus*.

The above-described method according to the invention and the comparison method are compared to the standard saturated steam method in the following Table 1.

TABLE 1

|  | Standard saturated steam (not inventive) | Steam/air mixture (not inventive) | Steam/air mixture and additional pressure loading (inventive) |
|---|---|---|---|
| Temperature [° C.] | 121 | 123 | 123 |
| Relative pressure [bar] | 1 | 2.3 | 2.3 (2.6)[2] |
| Time | 15 | 13 | 13 |
| $F_0$ value | 15[1] | 15.5 | 18 |

[1]per definition
[2]after pressure loading in second stage

It can be seen that the method according to the invention can, in a shorter amount of time, achieve a significantly better reduction in germs. Hence, the method according to the invention allows improved use of the energy contained in the steam in a simple and efficient manner.

The invention claimed is:

1. A method for thermal sterilization of a medical container filled with a liquid or flowable medical material or product, wherein the method comprises a sterilization step where a container filled with a medical material or product is subjected to a thermal sterilization in the presence of a sterilization atmosphere containing steam, at temperatures of at least 100° C. and at an increased pressure,
   wherein the sterilization step is preceded by a heating step;
   wherein the sterilization step is carried out in a relative pressure range of between 0.05 and 10 bar or in an absolute pressure range of between 1.05 bar and 11 bar;
   wherein the sterilization step comprises at least a first stage and a second stage following the first stage,
   wherein the first and second stages are each carried out at different pressures with respect to one another, wherein the pressure in the second stage is increased relative to the pressure in the first stage,
   wherein the relative pressure increase from the first to the second stage of the sterilization step is at least 0.01 bar and
   wherein the pressure increase from the first to the second stage of the sterilization step is effected by introducing air; and
   wherein the sterilization is followed by a cooling step wherein during the cooling step, a supporting pressure is applied at least temporarily, such that the pressure present in the medical container filled with medical material or product is counteracted.

2. The method according to claim 1, wherein the sterilization step is carried out in the presence of a steam/gas mixture.

3. The method according to claim 2, wherein the steam/gas mixture comprises a mixture of steam with at least one of nitrogen, oxygen and inert gases.

4. The method according to claim 1, wherein the method is carried out in a closed sterilization apparatus.

5. The method according to claim 1, wherein the method is carried out in an autoclaving apparatus.

6. The method according to claim 1, wherein the sterilization atmosphere is produced by injecting steam/compressed air mixtures into the sterilization apparatus.

7. The method according to claim 6, wherein the steam is produced from distilled or demineralized water and wherein the compressed air is produced from sterile air.

8. The method according to claim 1, wherein the sterilization step is carried out in a temperature range of between 100 and 180° C.

9. The method according to claim 1, wherein the sterilization step is carried out in a temperature between 110 and 130° C.

10. The method according to claim 1, wherein the sterilization step is carried out in a relative pressure range of between 0.1 and 4 bar or in an absolute pressure range of between 1.1 and 5 bar.

11. The method according to claim 1, wherein the sterilization step comprises 2 to 10 stages, wherein at least 2 stages are carried out at different pressures, with the pressure being increased in a subsequent stage compared to the pressure in a preceding stage.

12. The method according to claim 1, wherein, at least during the sterilization step, the method is controlled and monitored by measuring and regulating at least one of pressure and temperature of the sterilization atmosphere and optionally the temperature of at least one reference sample situated in the sterilization apparatus.

13. The method according to claim 1, wherein, at least during the sterilization step, at least one of pressure and temperature of the sterilization atmosphere and optionally the temperature of at least one reference sample situated in the sterilization apparatus are determined and set to predetermined values.

14. The method according to claim 13, wherein the pressure and temperature data are used to monitor and to control at least the sterilization step.

15. The method according to claim 1, wherein, during the heating step, at least one of pressure and temperature of the atmosphere within the sterilization apparatus is modified.

16. The method according to claim 1, wherein, during the cooling step, at least one of pressure and temperature of the atmosphere within the sterilization apparatus is modified.

17. The method according to claim 1, wherein the medical material or product is a medicine, a pharmaceutical or medical product.

18. The method according to claim 1, wherein the medical material or product is a catheter lubricant.

19. The method according to claim 1, wherein the container is an ampoule, a tube or a medical instrument.

20. The method according to claim 1, wherein the container is a catheter or a syringe.

* * * * *